United States Patent [19]

Eufinger et al.

[11] Patent Number: 5,798,924
[45] Date of Patent: Aug. 25, 1998

[54] PROCESS FOR PRODUCING ENDOPROSTHESES

[76] Inventors: Harald Eufinger, Goyer Busch 5, D-44803 Bochum; Lothar Heuser, Im Pastoratsbusch 49, D-44797 Bochum; Dieter Kruse, Königsberger Strasse 3, D-58455 Witten; Egbert Machtens, Bommerholzer Weg 31, D-5800 Wetter; Hans Seifert, Oenekinger Weg 97, D-58509 Lüdenscheid, all of Germany

[21] Appl. No.: 652,601

[22] PCT Filed: Dec. 2, 1994

[86] PCT No.: PCT/EP94/04020

§ 371 Date: Aug. 5, 1996

§ 102(e) Date: Aug. 5, 1996

[87] PCT Pub. No.: WO95/15131

PCT Pub. Date: Jun. 8, 1995

[30] Foreign Application Priority Data

Dec. 4, 1993 [DE] Germany ............... 43 41 367.6

[51] Int. Cl.$^6$ ............... G06F 19/00; G06G 7/64; G06G 7/66
[52] U.S. Cl. ............... 364/468.24; 364/468.03; 364/468.25; 364/474.24; 364/512
[58] Field of Search ............... 364/468.28, 468.04, 364/468.24, 468.25, 474.05, 474.24, 512, 468.03, 468.01, 468.26, 474.2; 623/20, 18, 21, 22, 23, 66, 2, 137; 137/512.1, 527; 128/653, 303

[56] References Cited

U.S. PATENT DOCUMENTS

| | | | |
|---|---|---|---|
| 4,791,934 | 12/1988 | Brunnett | 128/653 |
| 4,821,214 | 4/1989 | Sederberg | 364/522 |
| 4,822,365 | 4/1989 | Walker et al. | 623/20 |
| 5,026,391 | 6/1991 | McQueen et al. | 623/2 |
| 5,121,333 | 6/1992 | Railey et al. | 364/474.05 |
| 5,131,844 | 7/1992 | Marinaccio et al. | 433/72 |
| 5,351,196 | 9/1994 | Sowar et al. | 364/474.24 |
| 5,355,448 | 10/1994 | Uchino | 395/150 |
| 5,370,692 | 12/1994 | Fink et al. | 623/16 |
| 5,524,198 | 6/1996 | Matsumoto et al. | 395/157 |

FOREIGN PATENT DOCUMENTS

| | | |
|---|---|---|
| 093869 | 3/1983 | European Pat. Off. . |
| 097001 | 6/1983 | European Pat. Off. . |
| 146491 | 6/1985 | European Pat. Off. . |
| 255797 | 2/1988 | European Pat. Off. . |
| 387981 | 9/1990 | European Pat. Off. . |
| 451875 | 10/1991 | European Pat. Off. . |
| 456103 | 11/1991 | European Pat. Off. . |
| 551543 | 7/1993 | European Pat. Off. . |
| 574098 | 12/1993 | European Pat. Off. . |
| 2690836 | 11/1993 | France . |
| 3320395 | 12/1984 | Germany . |
| 2210707 | 6/1989 | United Kingdom . |
| 241362 | 8/1991 | United Kingdom . |

*Primary Examiner*—Reba I. Elmore
*Assistant Examiner*—Ramesh Patel
*Attorney, Agent, or Firm*—Collard & Roe, P.C.

[57] ABSTRACT

A process for producing endoprosthesis has the data block of a three-dimensional actual model (10) of the existing bone structure of a patient acquired using CT scanning. In a computer the actual model (10) thus determined is subtracted from the data block of an existing or CT scan-generated three-dimensional reference model (14). Then from the difference a computer-internal model for the endoprosthesis is formed. With this process, it is possible to reduce the work required for making the corrective adaptation of the endoprosthesis and to avoid faulty adaptations. The data blocks of the actual model (10) and reference model (14) are converted into the data of a CAD free form surface geometry. This is done by describing the limiting surfaces of the models through Spline and Bezier functions oriented to points of support and are imaged, and superimposed, on the computer monitor. This imaging is used to take back segments of the interface (11) of the actual model (10) by displacing points of support toward the volume of the reference model (14).

3 Claims, 6 Drawing Sheets

PROCESS FOR PRODUCING ENDOPROSTHESES

BACKGROUND OF THE INVENTION

1. Field of the Invention

The invention relates to a process for producing endoprostheses, in particular individually constructed implants and augments for reconstructive head surgery, in which process the data block of a three-dimensional actual model of the existing bone structure of a patient is acquired by means of computer-tomography, the actual model so determined is subtracted in a computer from the data block of an existing or computer-tomographically acquired three-dimensional should-be model, and a computer-internal model is formed for the endoprosthesis from the difference of the data blocks, which model is adapted on the video screen of the computer to the special anatomical features of the patient by an interactive manipulation of the data, and whose data block is finally used for the computer-controlled manufacture of the endoprosthesis.

2. The Prior Art

Similar methods which, however, do not comprise any corrective adaptation to the special anatomical features of the patient through an interactive manipulation of the data block, are known, for example from EP 0 255 797 B1; EP 0 093 869 A1; EP 0 146 491 A2; or EP 0 097 001 A1. In connection with the methods known according to said state of the art, it is possible with the use of suitable methods generating high-resolution images to adapt such endoprostheses relatively accurately to the existing bone structure of the patient to be supplemented.

However, in the manufacture of endoprostheses for restoring or for filling up bone defects in the region of the facial or brain skull, in particular in the manufacture of augments for supplementing atrophied alveolar processes for making available a suitable base for dental prostheses, an exact adaptation of the surface of abutment of the endoprosthesis on the surface of the still-existing bone structure to be supplemented does not suffice. Even with a highly exact adaptation of the endoprosthesis to the existing surface, painful pressure phenomena occur, for example in the region of the exit points of the bone canals receiving the nerves, or, in the case of progressed atrophy, within the region of the exposed bone canals.

For said reason, the surface of the endoprosthesis has to be shaped within the region of contact with nerval structures in a manner deviating from the directly derived geometric form, by recessing such surface within said region of the surface. In this connection, the recessed surface areas have to change to the adjacent, not recessed surface areas with softly rounded transitions, with the endoprosthesis being supported in said nonrecessed areas on the existing bone structure.

A similar corrective adaptation of the endoprosthesis to special anatomical features of the existing bone structure is required if the surfaces of the existing bone structure and the ones of the endoprosthesis coming into contact with one another have undercuts and/or projections which, when the endoprosthesis it put into place, are in the way. Such undercuts and/or projections interfering with the surgical intervention have to be eliminated prior to surgery as well, by adapting the endoprosthesis.

Finally, recesses in the endoprostheses to be manufactured are required also within the region of other non-osseous anatomical structures of the head, for example within the region of the nasal cavaties and eye sockets, the lateral nasal cavities, the auditory meatus, the middle or inner ear, as well as of the base of the skull, and particularly of the endocranium.

According to the state of the art, the corrective adaptations and recesses on endoprostheses explained above are possible only by highly labor-intensive, manual after-working, for example by carving or milling. Such after-working by hand requires much experience and leads to unusability of the endoprosthesis if the adaptations are flawed.

A process for producing a hip joint prosthesis, which is insertable in the femur, is known from EP 0 093 869 A1, in which process the adaptation of the contours of the endoprosthesis to the special anatomical features of the patient is carried out on the video screen of the computer by means of a covering pen or an electronic writing pen. The data representing the individual layer images of the endoprosthesis are changed (manipulated) as needed and stored with said aids. Based on the stored data of the layer images manipulated in said way, the computer is then capable of computing the data block for a three-dimensional model. In the manufacture of the endoprosthesis, the prosthesis manufacturing machine is then controlled on the basis of said data block.

The computer-assisted construction and adaptation of endoprostheses known according to said state of the art is highly labor-intensive and complicated and permits in all cases only a rough adaptation of the endoprosthesis to the bone structures existing on the side of the patient. Such rough adaptation is entirely sufficient, for example for orthopedic hip joint prostheses because with such prostheses, the outer surface of the prosthesis coming to rest against the inside wall of the hollow space of the bone, such space having been created artificially by scraping out spongiosa, is provided with steps, which are intended in order to effect an enhanced introduction of the static and dynamic forces into the bone. For said reason, the contours of the steps there in the successive horizontal planes need to be only approximately adapted to the curce of the borderline surface between spongy and compact matter.

As opposed to orthopedic prostheses, with endoprostheses for head surgery, the introduction of static and dynamic forces matters less than a corrective adaptation of the curves of the surface, leaving free sensitive nerval structures of the surface of the bone. Simple layer representation and manually made changes in the contours of the individual layer images no longer suffices with such corrective adaptation. Particularly if the contours of the individual sectional lines were corrected layer by layer, it would be very difficult to have the recessed surface areas change with softly rounded transitions to the adjacent, unrecessed surface areas, where the endoprosthesis is supported on the existing bone structure.

SUMMARY OF THE INVENTION

Therefore, the object of the invention is to further develop the process of the type specified above in a way such that the expenditure of labor required for the corrective adaptation of the surfaces of the endoprosthesis is reduced, and provision is automatically made for softly rounded transitions between the recessed surface areas and the adjacent, nonrecessed surface areas.

For achieving this object, the invention proposes on the basis of the process of the type specified above that the data blocks of the actual model and of the reference model are converted into the data of a CAD free-form surface geometry describing the limiting surfaces of the models through spline and Bezier functions oriented to points of support, and are imagined on the video screen of the computer disposed one on top of the other, and that based on such imaging, part areas of the interface of the actual model are recessed by displacing points of support in the direction of the volume of the reference model.

The hollow spaces formed through computer technology by displacing part areas of the interface of the actual model are cleared from the volume of the reference model in the mechanical manufacture of the bone implant. In the later implantation of the augment, said hollow spaces thus are in exactly the sites where the adaptation was made.

The process according to the invention has the advantage that the expenditure of labor for the corrective adaptation is extraordinarily low even in connection with highly complicated structures, and that in each adaptation process, the areas of transition between the recessed surface areas and the nonrecessed surface areas are quasi automatically softly rounded.

This has to be attributed to the fact that in the process according to the invention, the limiting surfaces of the models are represented in a free-form surface geometry, in which the surfaces are described by Spline and Bezier functions oriented on points of support. In this way, the limiting surfaces in a way become coherent, spatial structures, whose manipulations carried out locally at points of support have effects on all surfaces adjoining such point of support, whereby provision is automatically made that the surface areas changed by the point-of-support displacement change continuously and softly rounded to the adjacent, nonrecessed surface areas.

Especially the creation of such soft transitions is extremely important in connection with endoprostheses for head surgery, and can be accomplished only poorly and laboriously with the measures known for said purpose according to the state of the art.

The final shaping and fine adaptation of the new interface curve formed by the recession is usefully supported by reflection, elongation, turning or smoothing. Said manipulation functions make it possible to also finally finely adapt the prosthesis to the computer-internal model already in the computer, so that also the fine adaptations are already taken into account in the manufacture of the prosthesis.

The process according to the invention is particularly suitable for the manufacture of implants or augments in maxillary surgery. However, it can be applied also for other sensitive regions of bone construction, for example for the construction of individual implants of parts of the skull for eliminating osseous continuity defects following temporoparietal trepanation.

In particular, the process according to the invention has the advantage that the endoprosthesis can be directly produced with all special features to be taken into account. After-working or manual fine adaptation is no longer required. Another advantage consists in that the treatment time during the surgical intervention can be clearly reduced.

Additional advantages are obtained if a high-resolution computertomograph with helical data collection is used for the data acquisition. In said image-generating process, the part of the body of the patient to be acquired in terms of data is acquired by a helical spiral, the pitch of which is predetermined by the feed of the table per revolution of the X-ray tube.

The entire patient volume detected by the spiral can be subsequently reconstructed again layer by layer in accordance with conventional computertomographical representation, whereby the spacing of such reconstructed layers is not predetermined by the pitch of the spiral, but, for example, can be selected also smaller.

In view of the process of the type specified above, in which the exactness of the geometric adaptation of the endoprosthesis to the bone structure of the patient is limited only by the validity of the processed computertomographical data, two important indispensable advantages are obtained through the use of such a computertomograph as compared to other computertomographical acquisition methods:

(1) The rapidity of the data recording of about 20 seconds, i.e., quasi during one single breathhold, assures a minimizing of artefacts of motion on side of the patient, which could be recognized and corrected only with difficulty in the subsequent reconstruction process.

(2) The detection of a volume instead of individual surfaces (layers) permits the computer-internal reconstruction of a geometric model combined with the best possible aquisition of intermediate later regions; as opposed to conventional computer-tomographical techniques, a complete loss of information is avoided, or a loss of information increasing in the central direction is avoided in the case of adjoining or overlapping layer expanse in connection with a geometrically quasi concave bundle of X-rays.

BRIEF DESCRIPTION OF THE DRAWINGS

An exemplified implementation of the process according to the invention is explained in greater detail in the following by reference to the drawings, in which.

DETAILED DESCRIPTION OF PREFERRED EMBODIMENTS

Figure 1:
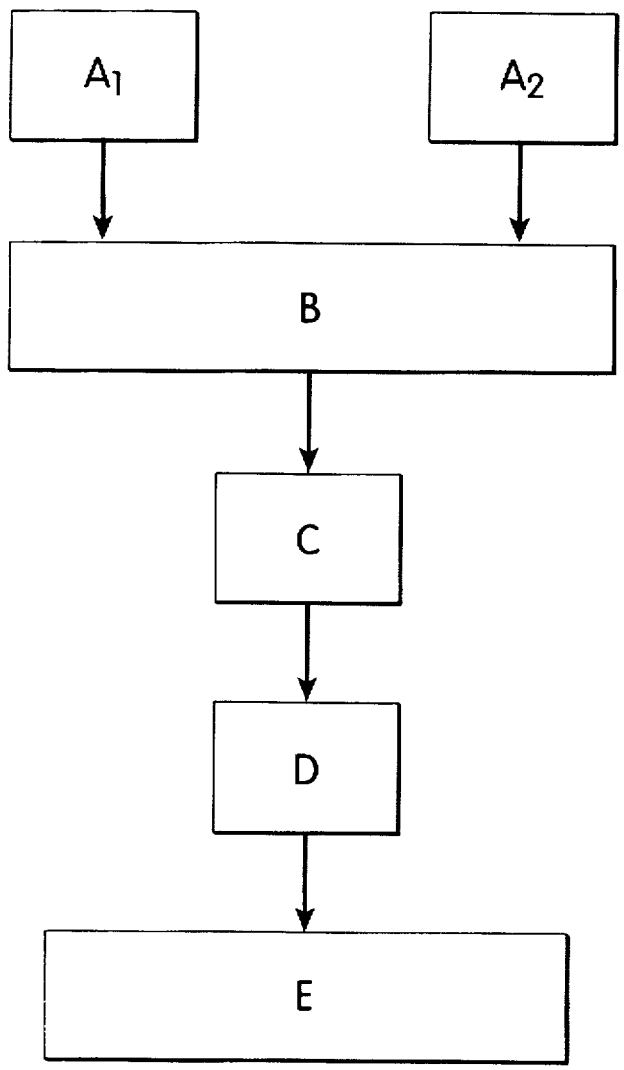
FIG. 1 schematically shows in a block diagram the process steps of the process according to the invention.

FIG. 1 schematically shows the sequence of the process for producing an endoprosthesis according to the invention. In process step A1, the data block of the actual model is first acquired computertomographically on the lower jaw of the patient to be treated. At the same time, the data block of the reference model is made available at position A2. Said data block is available either in a suitable storage medium or it is also acquired computertomographically from a physically existing reference model.

In process step B, the data blocks of the actual model and of the reference model are converted computer-technologically into the data unit CAD free-form surface geometry, which is a three-dimensional representation of the limiting surfaces of the models which is oriented on points of support, such limiting surfaces being described by numerical Spline and Bezier functions. The surface structures in said representation are characterized in that they can be easily handled by interactive CAD-modeling and manipulating methods.

In the subsequent process step C, the converted data blocks of the actual model and of the reference model are shown superimposed on the video screen. Based on this image, part areas of the interface of the actual model are displaced by an interactive CAD modeling and manipulating method in the direction of the volume of the reference model. Recesses and hollow spaces are produced in this way in the regions of the endoprosthesis where no contact is desired with the existing bone structure. Likewise, projections and/or undercuts of the endoprosthesis to be produced can be removed, which can be seen in advance to pose problems when the endoprosthesis; is inserted.

Finally, in process step D, the difference of the data of the actual and reference models is formed, and a data block is generated in this way which can serve as the model for the computer-assisted manufacture of the endoprosthesis.

Based on said data block, the finished endoprosthesis is finally produced in process step E with the help of a computer-controlled manufacturing unit.

Figure 2:
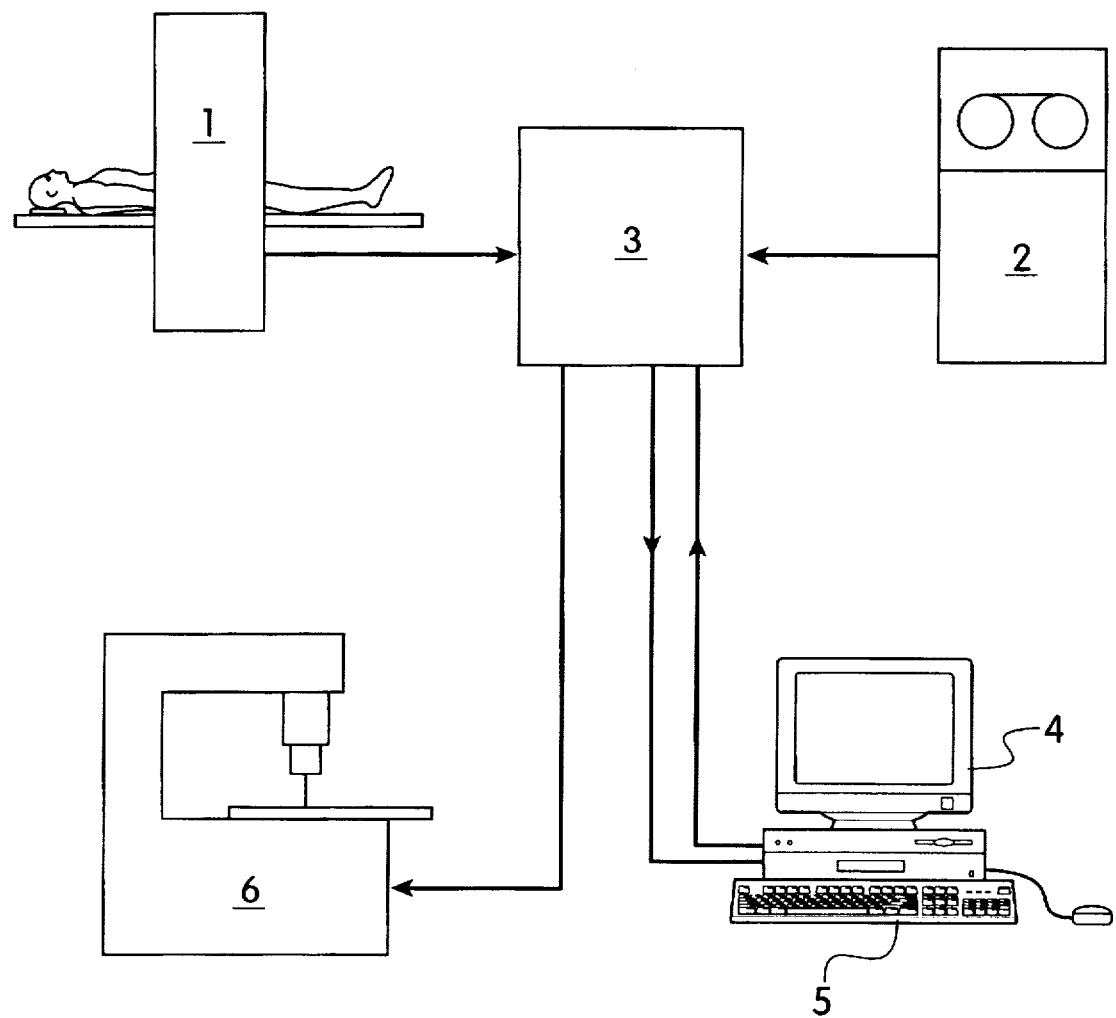
FIG. 2 shows an equipment configuration for carrying out the process according to the invention.

The equipment configuration shown in FIG. 2 has a computertomograph 1 with helical data acquisition. Said computertomograph serves for acquiring the data of the actual model on the patient. The data of the reference model are either acquired in the computertomograph 1 on the basis of a physically existing reference model as well, or such data are available in a suitable data mass memory 2. For converting the acquired or made-available data blocks of the actual model and the reference model into the data of a CAD free-form surface geometry and for the subsequent manipulation of said data, use is made of a suitably efficient computer 3, which is equipped with a video screen 4 and with the usual digital and/or graphical input unit 5.

The final formation of the difference for generating the computer-internal model for the endoprosthesis to be produced takes place in the computer 3 as well.

Finally, the endoprosthesis is produced in a computer-controlled manufacturing unit 6.

Figure 3:
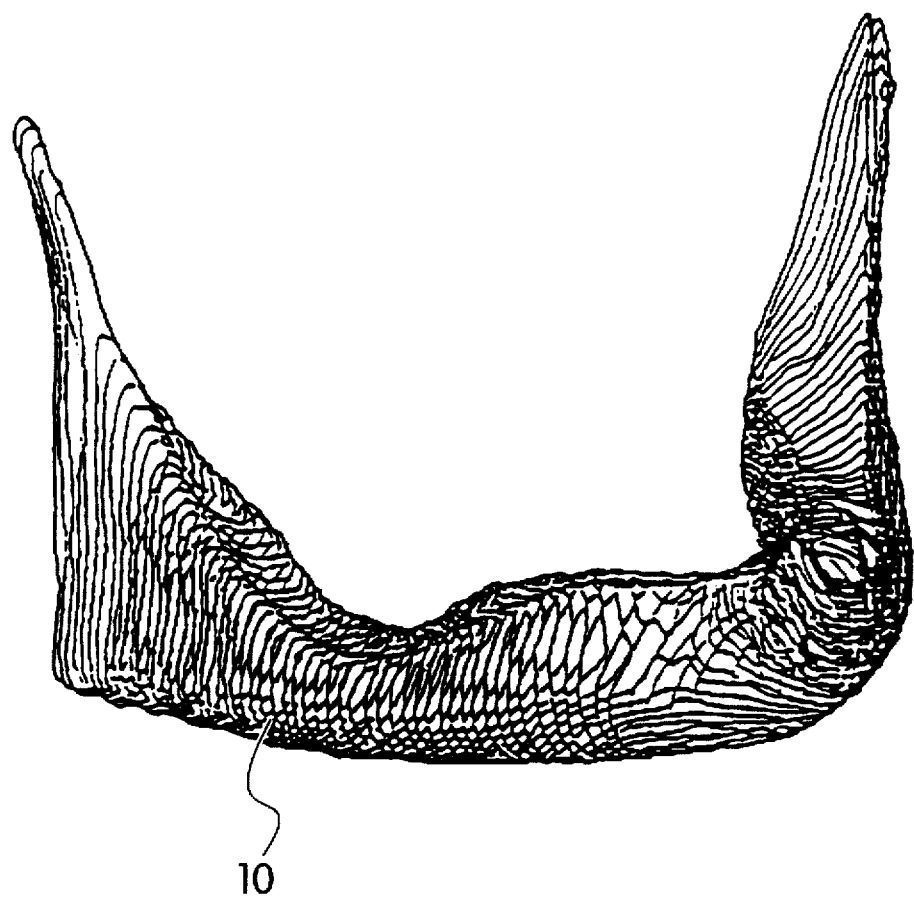
FIG. 3 shows the idealized free-form surface geometry of an atrophied lower jaw as an actual model shown by a perspective view.

FIG. 3 shows a printout of a representation of the actual model 10 as it is shown on the video screen 4 in process step C.

Figure 4:
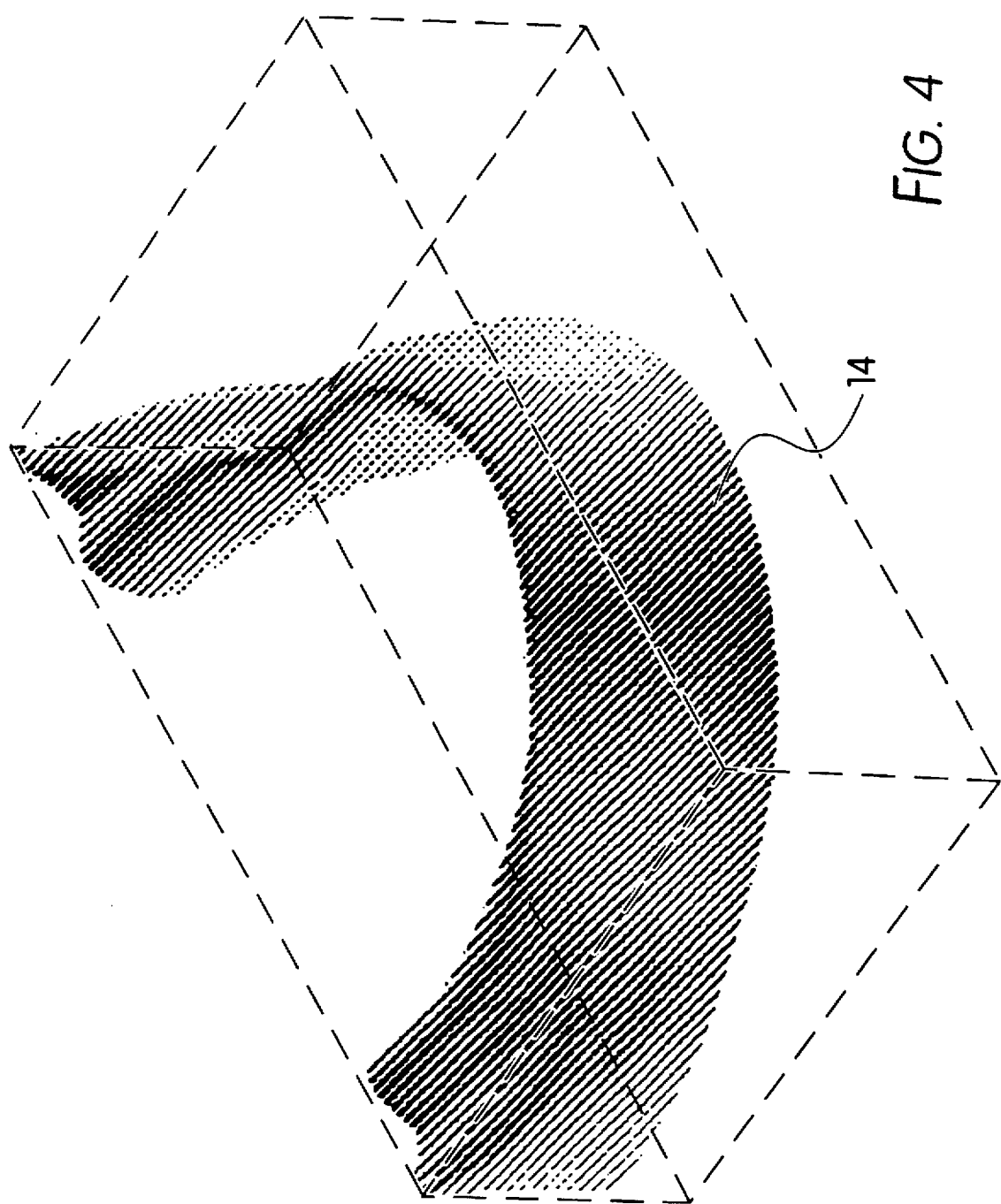
FIG. 4 shows the idealized free-form surface geometry of a comparative model shown as the reference model in a perspective view.

FIG. 4 shows the reference model 14 by the same representation.

Figure 5:
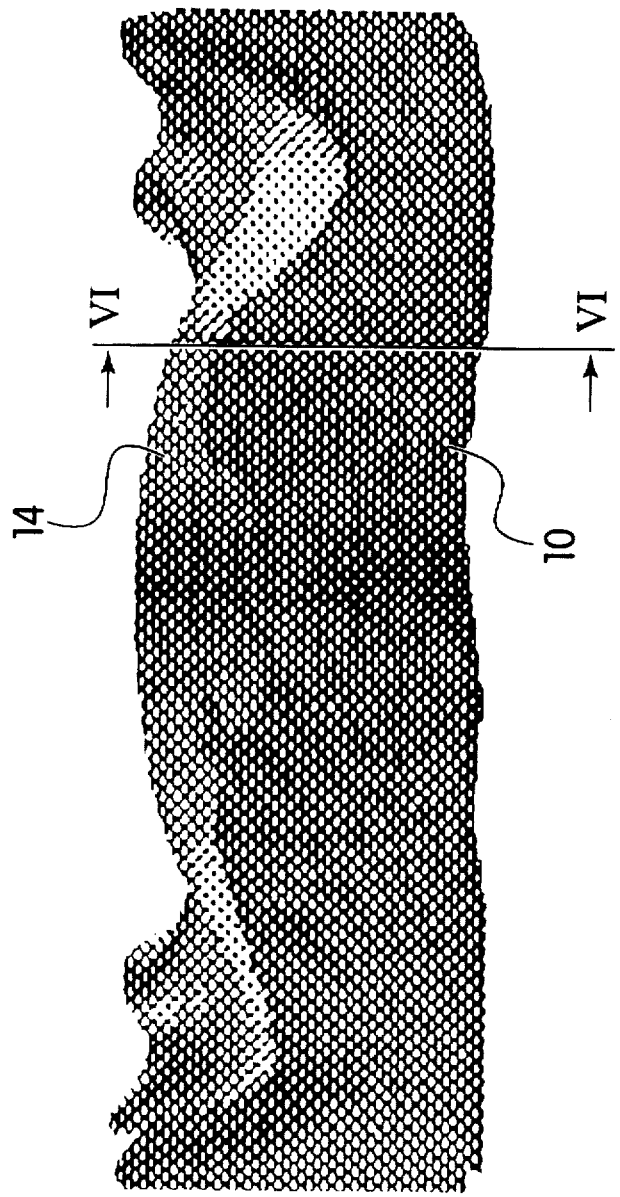
FIG. 5 shows the presentation of the superimposition of FIGS. 3 and 4 on the video screen.

In FIG. 5, the actual model 10 according to FIG. 3 and the reference model 14 according to FIG. 4 are shown superimposed. In said representation on the video screen 4, the two models are usefully shown in different colors, so that they can be better distinguished from each other. It is possible to place through the two superimposed models 10 and 14 any desired sections, on the basis of which the adaptation and the subsequent fine adaptation is made in the critical sites. The adaptation essentially takes place by support point displacement The fine adaptation is accomplished by geometric manipulation functions (reflecting, expending, turning, rounding, smoothing etc.). The adaptation is made in a way such that the height and position in the direction of the sagittal and transversal planes as well as the recesses of exit regions of the sensitive nerves of the lower jaw are adapted to the shape of the endoprosthesis to be produced. The well-rounded shape and the sweeping curve of the sagittal plane orientation (compensation curve) of the endoprosthesis to be produced are obtained already in advance through the reference model 14 shown in FIG. 4.

Figure 6:
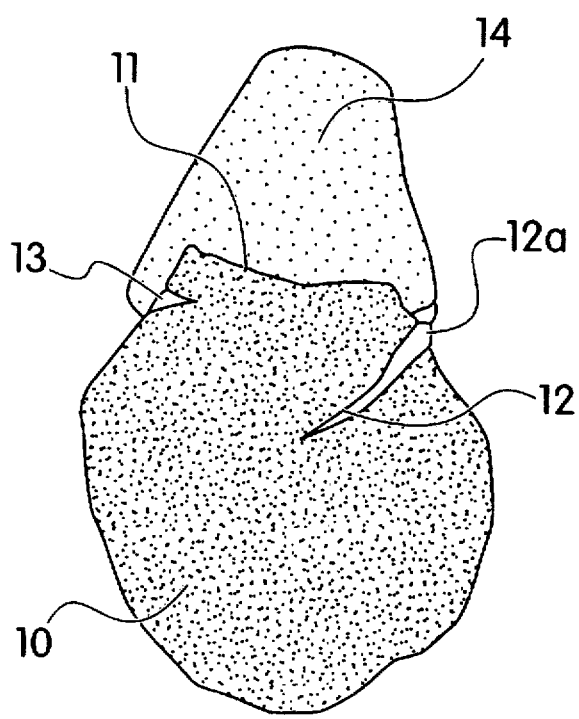
FIG. 6 shows the representation of a vertical section along line 6—6 in FIG. 5.

A section along line 6—6 in FIG. 5 is shown in FIG. 6. In the latter figure, the cross section of the actual model 10 with its interface 11, the bone canal 12 and an undercut 13 is shown by dark hatching, whereas the cross section of the reference model 14 is shown by light hatching. FIG. 6 shows that the interface 11 of the actual model 10 has been displaced within the region of the exit 12a of the bone canal 12 and the undercut 13 into the volume of the reference model 14. The cross sectional surfaces of the reference model that have become exposed due to the displacement are not hatched. Following the formation of the difference between the actual model 10 and the reference model 14, recesses or cavities are created within the range of the unhatched areas; in the range of such recesses or cavities, the manufactured endoprosthesis does not rest against the surface of the bone structure of the patient (=actual model).

We claim:

1. Process for producing endoprostheses, in particular individually constructed implants and augments for reconstructive head surgery, in which the data block of a three-dimensional actual model of the existing bone structure of a patient is acquired by means of computertomography,the actual model so acquired is subtracted in a computer from the data block of an existing or computertomographically acquired, three-dimensional reference model, and a computer-internal model for the endoprosthesis is formed based on the difference of the data blocks, said model being adapted on the video screen of the computer by interactive manipulation of the data to the special anatomical features of the patient, and the data block of such model being finally used for the computer-controlled manufacture of the endoprosthesis, comprising converting the data blocks of the actual model (10) and of the reference model (14) into the data of a CAD free-form surface geometry describing the limiting surfaces of the models by Spline and Bezier functions oriented to the points of support, and shown as superimposed imaging on the video screen of the computer; and that based on said imaging, part areas of the interface (11) of the actual model (10) are recessed by support-point displacement in the direction of the volume of the reference model (14).

2. Process according to claim 1, wherein the final shaping and fine-adaptation of the new curve of the interface created by recession is supported by reflecting, expanding, rounding or smoothing.

3. Process according to claim 1, wherein a high-resolution computertomograph (1) with helical data collection is used for the data acquisition.

* * * * *